United States Patent
Van et al.

(10) Patent No.: US 6,546,820 B1
(45) Date of Patent: Apr. 15, 2003

(54) METHOD AND APPARATUS FOR MULTIFUNCTION VACUUM/NONVACUUM ANNEALING SYSTEM

(75) Inventors: Phuc Van, San Jose, CA (US); Yuen Lim, San Jose, CA (US)

(73) Assignee: Ann F. Koo, San Jose, CA (US)

( * ) Notice: Subject to any disclaimer, the term of this patent is extended or adjusted under 35 U.S.C. 154(b) by 0 days.

(21) Appl. No.: 09/502,168

(22) Filed: Feb. 11, 2000

(51) Int. Cl.[7] ............................................... G01R 31/26
(52) U.S. Cl. ...................................................... 73/865.8
(58) Field of Search .............................. 73/865.6, 865.8, 73/866, 863.11, 863.12, 28.01; 374/45, 57, 47, 49, 51; 324/693, 228, 760, 761; 356/300, 311, 327, 323, 244, 503

(56) References Cited

U.S. PATENT DOCUMENTS

| | | | | |
|---|---|---|---|---|
| 1,888,755 A | * | 11/1932 | Barr et al. ..................... 73/791 |
| 4,874,952 A | * | 10/1989 | Arnaud et al. ............. 73/865.6 |
| 5,410,162 A | * | 4/1995 | Tigelaar et al. ............... 374/57 |
| 5,959,215 A | * | 9/1999 | Ono et al. ..................... 73/789 |
| 5,980,103 A | * | 11/1999 | Ikuno et al. .................. 374/57 |
| 5,999,267 A | * | 12/1999 | Zawaideh .................... 356/503 |
| 6,065,354 A | * | 5/2000 | Dinsmore .................. 73/865.6 |
| 6,108,087 A | * | 8/2000 | Nikoonahad et al. ....... 356/503 |
| 6,113,262 A | * | 9/2000 | Purola et al. ................. 374/57 |
| 6,191,599 B1 | * | 2/2001 | Stevens ....................... 324/760 |
| 6,215,324 B1 | * | 4/2001 | Yoshida ...................... 324/760 |
| 6,217,212 B1 | * | 4/2001 | Brenninger et al. .......... 374/45 |

* cited by examiner

Primary Examiner—Robert Raevis

(57) ABSTRACT

An apparatus is disclosed for in situ characterizing and quantifying physical properties of thin film materials over time and in various environments. Through the utilization of multiple probes and sensors, and the processing of the data, a rapid and accurate forecast of the material's behavior in a selected environment may be obtained. The present invention scans for a variety of properties, including film stress, film thickness, desorption, reflectivity, and resistivity. Photodetectors are used to collect reflected light which is processed by computer for analysis, while simultaneously processing data collected from the probes and sensors placed within and without the testing chamber. Data is collected and analyzed over time while sample materials are subjected to selected environments, including thermal cycling and gaseous or vacuum environments, using multiple probes according to the user's industry needs.

22 Claims, 11 Drawing Sheets

TOP VIEW

FRONT VIEW

METHOD AND APPARATUS FOR MULTIFUNCTION VACUUM/NONVACUUM ANNEALING SYSTEM

BACKGROUND OF THE INVENTION

The present invention relates generally to multifunctional testing of materials. More particularly, the present invention relates to the testing, processing, and process monitoring of materials used in the manufacture of integrated circuit chips for the semiconductor and optoelectronic industry.

With the impetus toward smaller and faster devices, semiconductor manufacturers increasingly require rapid discovery and implementation of new materials capable of providing greater performance, such as low k, high k, copper and other novel materials. However, several of these new materials are sensitive to oxidation at elevated temperatures, and additionally are prone to emit volatiles and particulates or exhibit property changes upon heating and cooling.

Thus, these new materials require testing to determine their usefulness in semiconductor processing. Conventionally, the processing, testing, and process monitoring of the thermal-mechanical properties of thin film materials requires the use of several complementary tools, each having a single function. Thus, several such tools are required to monitor the physical, chemical, or electrical properties of sample materials undergoing temperature changes. No single tool has conventionally been able to change functions to monitor, analyze and quantify multiple properties simultaneously during processing, especially thermal cycling.

Therefore, characterizing the stress hysteresis, thermal stability, out gassing, film shrinkage, thermal expansion coefficients, adhesion, and electrical properties of materials, where the data base is nonexistent or limited, conventionally requires the use of several complementary tool sets and the use of multiple samples. However, the use of several separate tools for testing, as is conventionally required, often introduces inconsistencies and errors in test results.

One error introduced when using separate testing tools is sample-to-sample error. Often a sample material is destroyed during testing. Thus, several identical samples are typically required since several separate tools are utilized for testing. Theoretically each tool tests the properties of an identical sample, with the results from the separate tools being correlated to determine the characteristics of the material. However, difficulties arise in creating "identical" samples, resulting in non-identical samples. Hence, each tool actually tests a different sample material, resulting in testing errors and error accumulation during later correlation of the data.

Another error introduced when using several separate testing tools is tool-to-tool errors. When testing different properties of a material with different tools, theoretically the engineer sets the testing environments for the various tools similarly, then tests the properties for which each particular tool is designed. However, as with creating "identical" material samples, problems arise when attempting to set "identical" testing environments on separate testing tools. Often the heating temperatures do not exactly match on different tools, or heating times may not be the same. In either case, testing is actually performed in non-identical testing environments, resulting in testing errors and error accumulation during later correlation of the data.

Thus, conventional material testing is greatly susceptible to errors because of the combined effects of errors caused by sample-to-sample variation and errors caused by tool-to-tool variation. Moreover, new material samples are often in limited quantity resulting in process conditions often being unrepeatable. Often, correlation of the various results to form a meaningful understanding of the problem at hand is next to impossible.

In view of the above, what is needed is a method and apparatus for testing materials wherein sample-to-sample error and environment-to-environment error can be reduced. The method should further enable a faster testing cycle, and allow for easy correlation of test results.

SUMMARY OF THE INVENTION

The present invention addresses the above mentioned needs by providing an integrated, multifunctional annealing system. The invention provides a system for monitoring, obtaining, and measuring physical characteristics of thin film materials. The system involves simultaneous scanning of the material with physical sensors, such as laser beams, and probes by proximity or contact, and correlating the obtained data to provide a database of thin film characteristics over time, temperature changes, and varying environments.

In one embodiment, an apparatus for simultaneously extracting multiple physical characteristics of materials is disclosed. The apparatus includes a housing and a chamber disposed within the housing that is capable of achieving multiple temperatures. At least two material characteristic sensors are also disposed within the housing for providing multiple sets of data concerning the characteristics of a sample material. Finally, a data correlator coupled to the sensors correlates the first and second sets of data. Advantageously, the apparatus of the present invention reduces sample-to-sample error and tool-to-tool error encountered in conventional material characteristic testing.

In another embodiment, a method for simultaneously extracting and analyzing physical characteristics of materials is disclosed. The method comprises providing a housing and a chamber disposed within the housing that is capable of achieving multiple temperatures. A first set of physical properties of a sample material is then sensed using a first sensor disposed within the housing. Next, a subsequent set of physical properties of the sample material is sensed using a different sensor disposed within the housing. Finally, the sets of physical properties are correlated, thus determining the material characteristics of the sample material.

Because thin film materials are oxidation sensitive, the process monitoring and testing of these films requires heating or annealing in a very low or no oxygen environment that is currently difficult to achieve with traditional high temperature stress tools. Advantageously, the present invention addresses this issue by being capable of operating in a controlled inert gas environment or an ultra high vacuum environment, thus making possible simulation of actual thermal processing. A further advantage of the present invention is its suitability for thermal desorption spectroscopy. Further, the chamber's circular highly reflective and controlled cooling walls allow radiant heat from a heating lamp source to be focused uniformly onto the sample material.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

An invention is disclosed for providing an improved in situ system for simultaneous extraction and quantification of physical properties of materials during thermal processing. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

The present invention provides a sealed heating type chamber that operates in an inert gas environment or a high/ultrahigh vacuum mode to emulate processing. Multiple probes or process monitoring devices inside the chamber, and devices capable of viewing or scanning the sample through openings in the chamber wall facilitate material testing during a programmed heating cycle. This configuration allows the present invention to process, monitor, and simultaneously extract chemical, optical, electrical, mechanical, particle, and other physical characteristics of a sample of material as it undergoes temperature and other environmental stimulations. These characteristics can be extracted either serially or simultaneously without the need for more than one sample. The present invention greatly reduces sample-to-sample and tool-to-tool variations, provides consistent data, and speeds up the characterization process, thus shortening process integration to market time.

Figure 1:
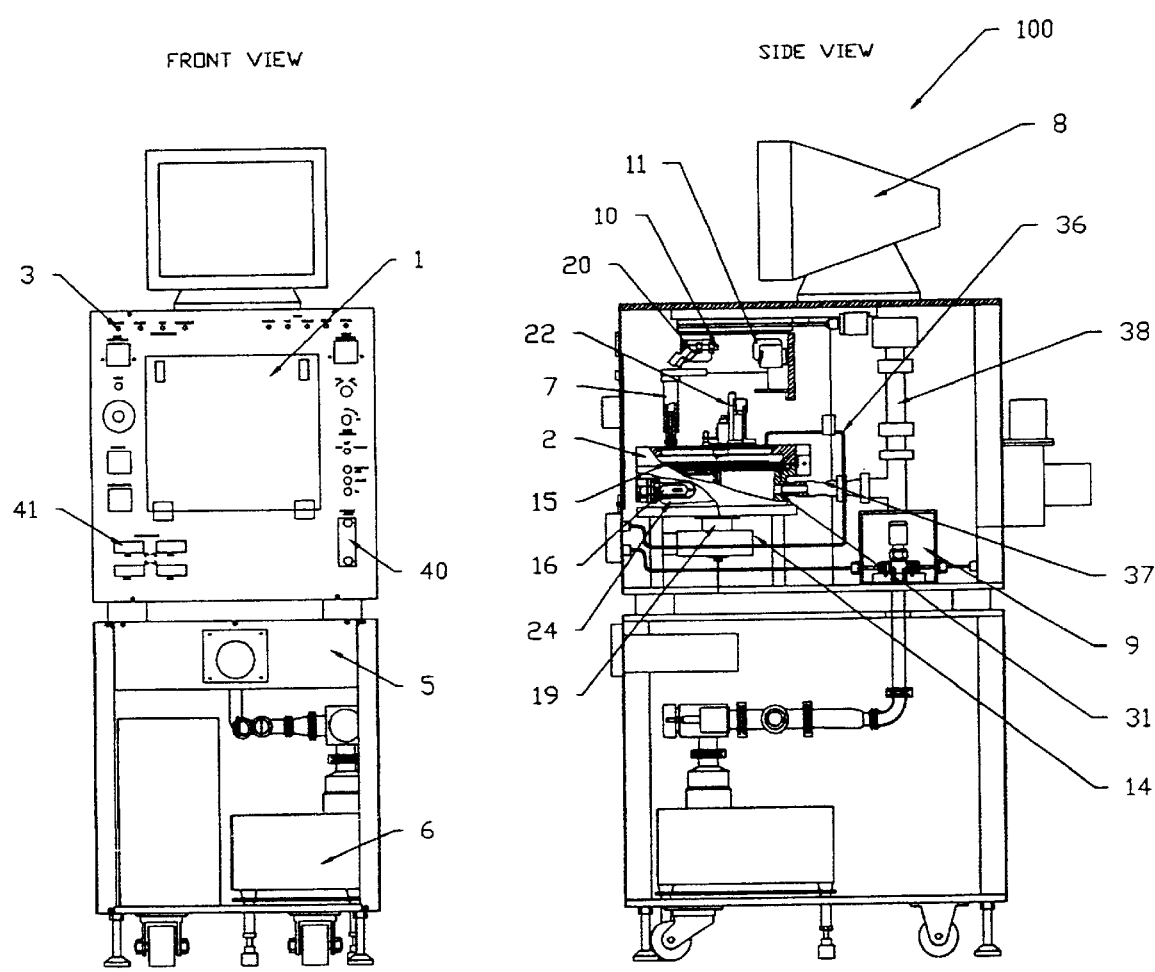
FIG. 1 shows a pictorial view of an apparatus for an improved system for simultaneous extraction and quantification of the physical properties of materials during thermal processing in a vacuum annealing chamber, in accordance with an embodiment of the present invention.

FIG. 1 is an illustration showing a front view and a side view of an integrated testing apparatus 100, in accordance with an embodiment of the present invention. The integrated testing apparatus 100 includes an upper platform housing with an access door 1 to a testing chamber body 2, a vacuum gauge 5, and a vacuum pump 6 having associated vacuum piping. The integrated testing apparatus 100 further includes a scanning assembly 11 having multiple probes including a surface scanner, a reflectivity scanner, a film thickness detector 7, multiprobes 22, a testing chamber body 2, halogen radiant heat lamps 16, susceptor 15, susceptor rotation mechanism 14, susceptor rotation mechanism adaptor 19, gas control valves 9, gas/vacuum mode selector 41, a gas purge flow indicator 40, a vacuum adaptor 37, a vacuum port 31 and a residual gas analyzer 38. Finally, system control is provided by a computer 8 connected to the integrated testing apparatus 100 by a ribbon interface cable.

Low k and copper thin films pose a characterization problem for metrology tools, like the traditional high temperature stress tool because these oxidation sensitive materials must be processed or annealed in an atmosphere with a very low oxygen atmosphere, in many cases, less than 10 ppm. This low oxygen criterion is impossible to achieve with traditional high temperature stress tools, because of their relatively open design. However, the present invention's chamber is designed to operate in a high vacuum environment or in a controlled inert gas environment where, at less than 10 ppm of oxygen. This permits ideal simulations of actual thermal processes.

Figure 2:
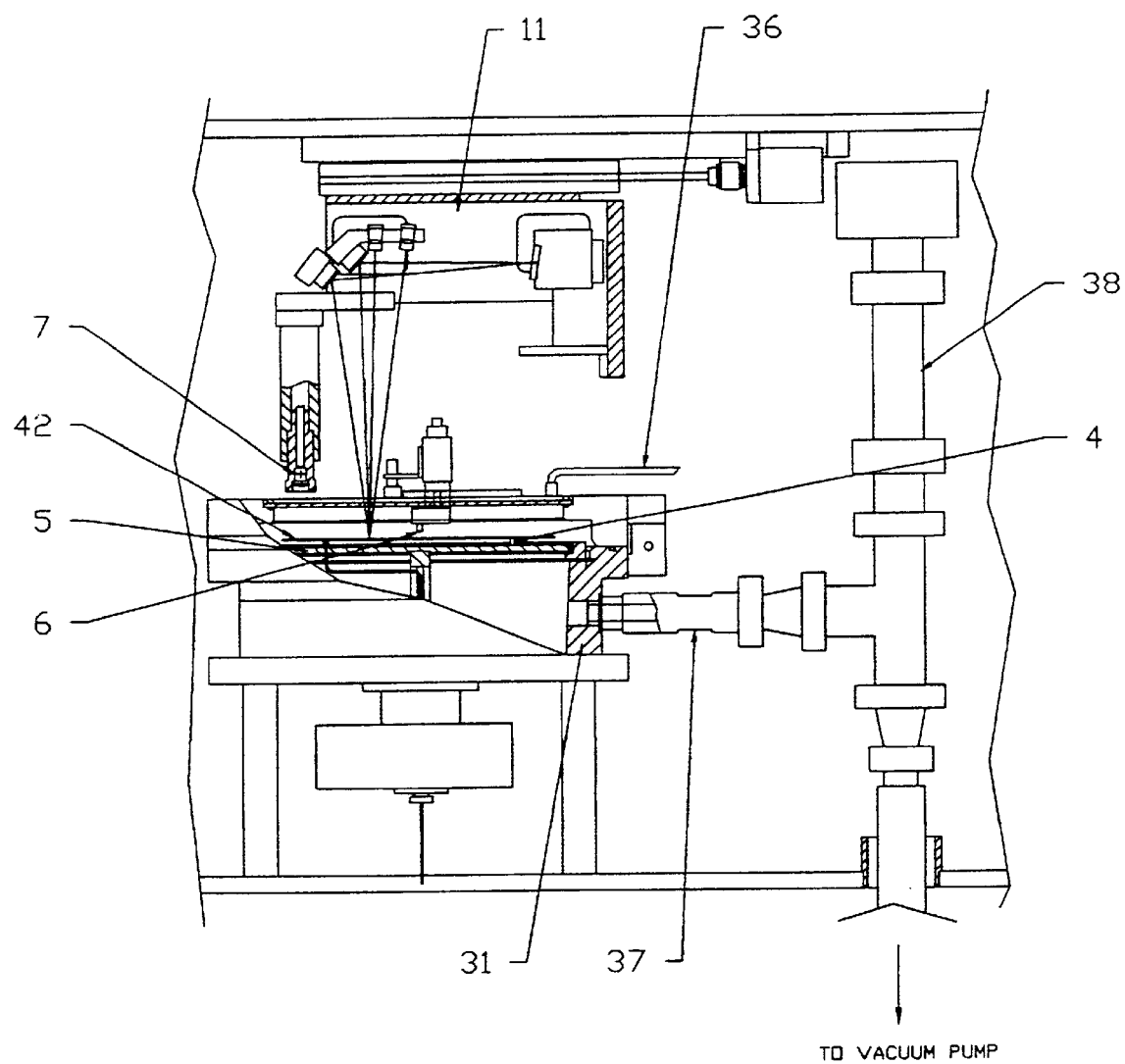
FIG. 2 is a pictorial view of the upper housing platform of the testing machine, in accordance with an embodiment of the present invention.

FIGS. 2 and 3 further illustrate the integrated testing apparatus of the present invention. In use, a silicon wafer is supported by a fixed or rotatable susceptor 15 made of quartz or a temperature stable material, supported and rotated by a quartz shaft 12, with an outer ring to insulate the susceptor and thus achieve temperature uniformity of the sample material. The susceptor is rotated by the susceptor stepper motor 25 through the rotation mechanism 14 which attaches to the chamber body by the rotation mechanism adaptor 19. A thermocouple is disposed within the susceptor shaft 20 and may be placed in close proximity to the wafer 26 and through a thermal couple support pin 13.

Scanning is performed optically through a clear quartz window 28. The optically clear window 28 is mounted within the chamber top plate 33 above the sample wafer for optical scanning by the scanner assembly 11, which houses the various detectors. The scanner detector assembly 11 employs a laser 10 to scan the sample wafer with a laser beam. Reflected radiation from the sample wafer is focused by the mirrors 20 to the scanner detector 11 for analysis by computer. The film thickness detector 7 detects radiation emitted by the wafer and sent to a spectrometer for analysis by computer.

A multiprobe 22, a generic probe that makes contact with the sample, is mounted through an access port 21 in the top plate of the chamber for physical testing of the sample wafer during cycling. Probes 23 may be placed in proximity to or in contact with the sample wafer for testing. Different properties are sensed through each of the probes 23 during testing.

A vacuum adaptor 37 is mounted between two heating lamps in the wall of the chamber body 2 at the vacuum port 31 providing a connection to the vacuum pump for a high vacuum environment.

A gas may be introduced into the testing chamber body to simulate a specific wafer processing environment, through gas lines 36 controlled by gas control valves 9 as dictated by the testing needs of the user. A residual gas analyzer 38 is attached to the chamber body to identify any residual gas in the vacuum system that may be emitted from the wafer.

Figure 3A:
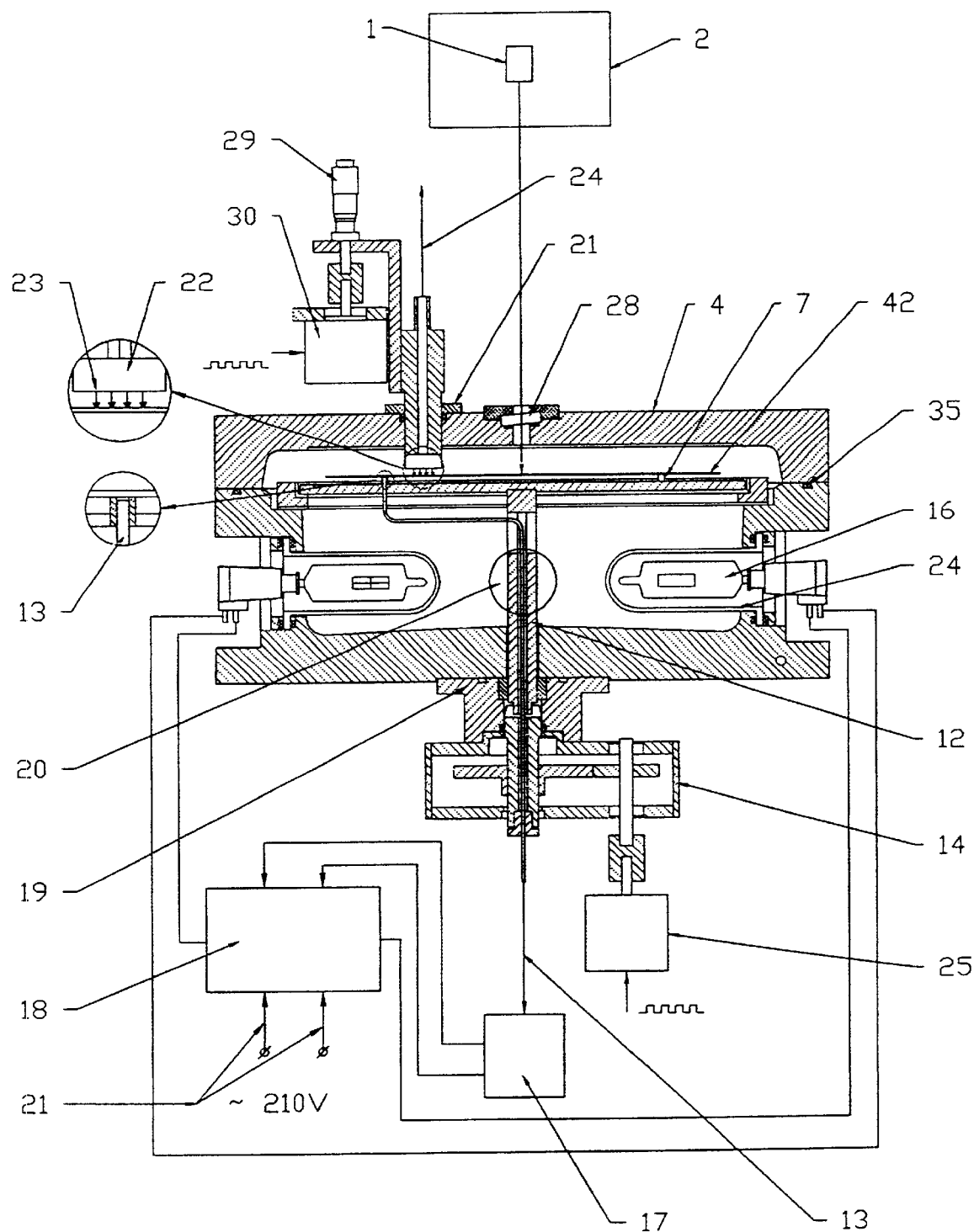
FIG. 3a is a pictorial view of the vacuum annealing chamber, in accordance with an embodiment of the present invention.
Figure 3B:
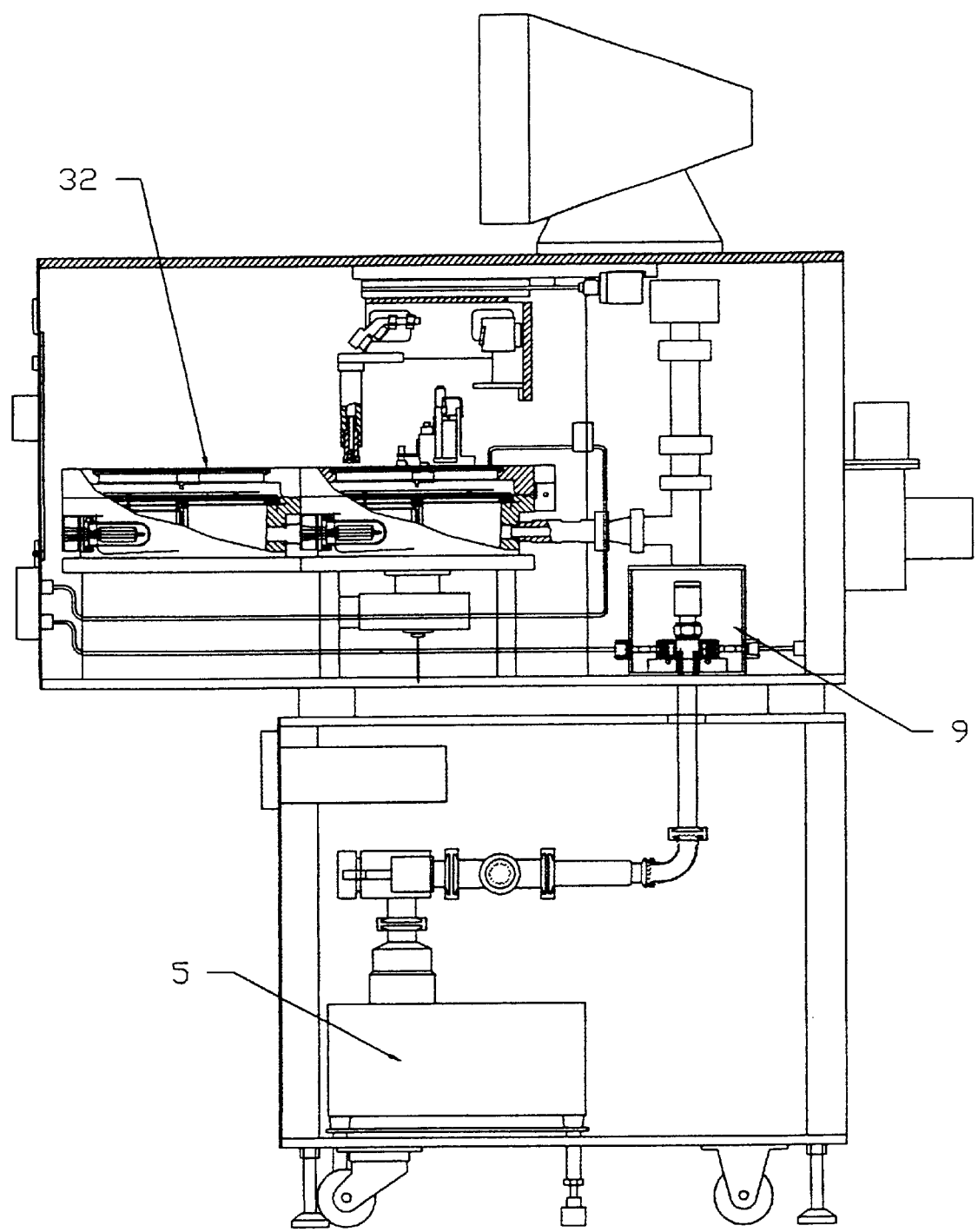
FIG. 3b is an illustration showing a vacuum annealing chamber having a load-lock mechanism, in accordance with an embodiment of the present invention.

FIG. 3a is an illustration showing an interior of a testing chamber, in accordance with an embodiment of the present invention. An additional feature of the chamber, not illustrated, is a highly reflective gold or rhodium plating of the interior wall surfaces of the chamber to ensure a clean, stable nonreactive environment, to maximize the effectiveness of the radiant heat transfer process, and to improve heating uniformity of the sample wafer. Halogen heating lamps 16 are mounted radially within the chamber walls below the susceptor and provide a focused radiant heat source for heating the sample wafer during testing. Each heating lamp is sealed and protected by a clear quartz lamp cover 24. Lamp heating is regulated by a proportional integral differential temperature controller 17. The thermocouple 13 senses the temperature and acts as a feedback to the proportional integral differential controller 17. There may be eight, ten or twelve lamps placed in the chamber, with sets of two lamps wired in series. The lamps are monitored by current meters 41 which measure the current flowing through each lamp and also detect broken lamps.

The sealed annealing type chamber of the present invention is based on a rapid thermal processing type chamber design. The system can operate either under high vacuum ranging up to 10–6 Torr or in a controlled inert gas environment to simulate device processes. By incorporating multiple metrology probes either inside the chamber or which can view the material sample inside the chamber, through a window, data like film stress hysteresis, thermal stability, thermal desorption spectroscopy, film shrinkage, reflectivity, resistivity and CV changes may be monitored in situ simultaneously.

A probe movement stepper motor 30 allows incremental vertical movement of the multiprobe 22 depending upon the thickness of the wafer and whether the testing is non contact or in contact with the wafer. In practice the incremental adjustments result in advancing or retracting the probe in incremental distances of about 5 microns.

The interior of the testing chamber body may be filled with a gas of the user choice or according to user processing environments. Gas enters through gas inlets 36 and is controlled by the gas valve controls 9 and is monitored by a gas flow meter 40.

In use, materials to be tested, such as silicon wafers, are introduced into the chamber by opening the chamber access door and placing the wafer on the susceptor manually. The closed chamber is then sealed by clamps 34 and vacuum o-rings 35. In another embodiment, shown in FIG. 3b, silicon wafers are introduced into the chamber mechanically through a load lock mechanism 32 during different environments, including, but not limited to, high temperature, high vacuum, or other specific gas environments without effect by the ambient environment which attains a temporarily similar environment as in the chamber.

Examples of materials to be tested can include broken, cut or whole silicon wafers of the semiconductor type, as well as non-semiconductors such as steel, ceramics, polymers, etc.

Figure 4:
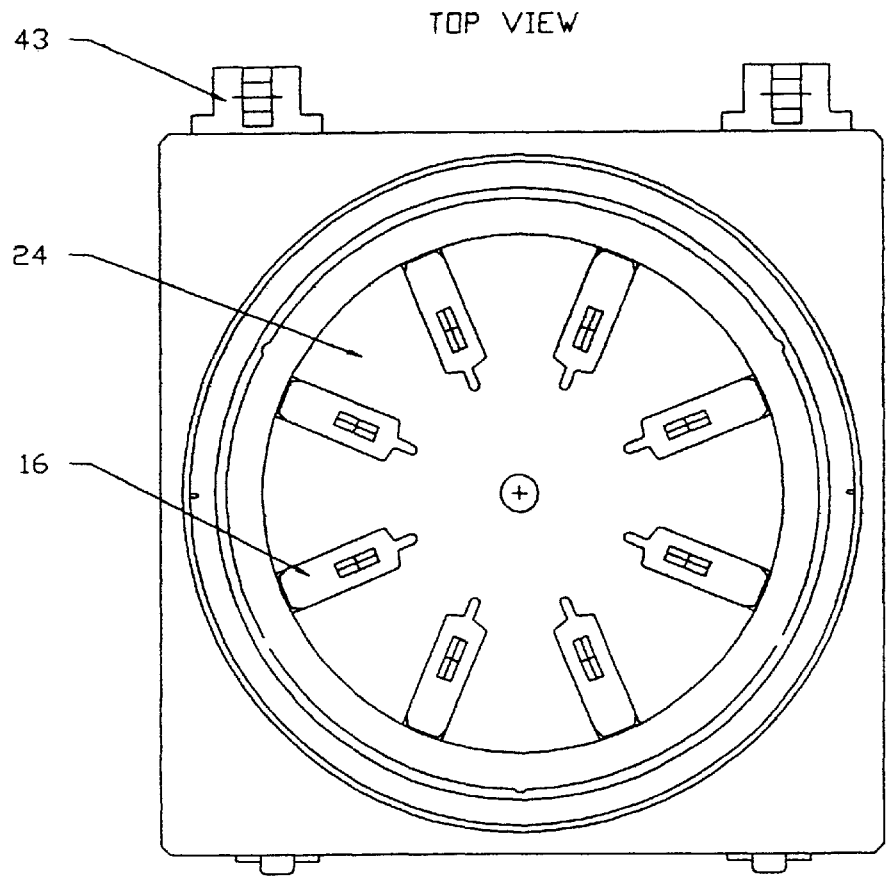
FIG. 4 is a pictorial view of the circular annealing chamber body with halogen heating lamps installed horizontally in the lower chamber body plate, in accordance with an embodiment of the present invention.
Figure 4:
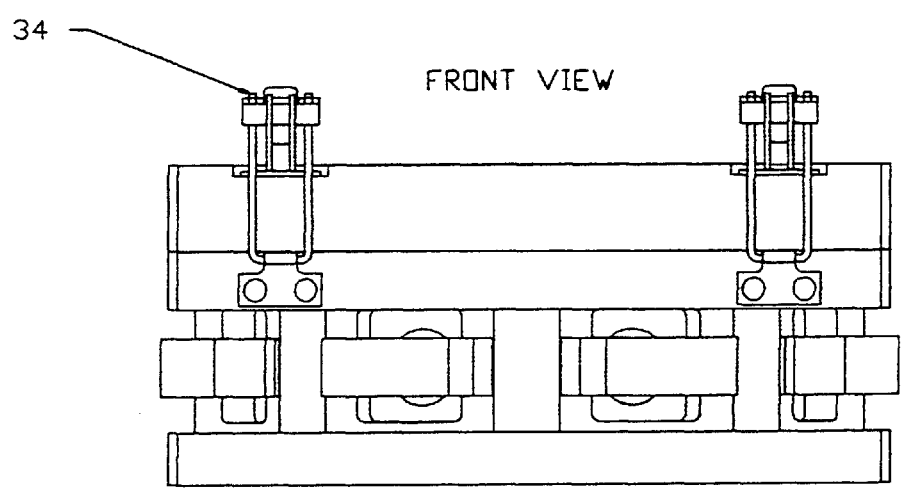

FIG. 4 illustrates the halogen lamp heating configuration in the chamber body. The chamber body has ten halogen lamps mounted radially in the interior walls of the lower chamber body plate. The halogen lamps may be placed on one side or both sides of the sample 42. Each lamp has a clear quartz cover sealing the lamp from the testing chamber environment. The lamps are positioned radially below the susceptor to promote heat transfer to the sample wafer being tested. Hinges 34 connect the upper body plate to the chamber body 2.

With a Class 1, clean room compatible, halogen lamp based heating system, the present invention offers versatile temperature ramping and annealing programming cycles. By using a computer to control heat intensity, multiple sensors and probes or monitoring devices, properties such as film stress, thermal desorption, film thickness, reflectivity, etc., can be simultaneously extracted, quantified and improved.

Most out gassing studies, such as thermal desorption spectroscopy, performed on the new low k materials are done on small broken pieces of wafers. The results may raise data correlation issues, as the tool may not simulate whole a wafer desorption under actual thermal processes. The invention is capable of testing whole wafers. Thermal desorption spectroscopy and the other metrology information, like stress hysteresis and in situ film shrinkage and reflectivity data can be collected simultaneously, avoiding sample to sample and tool to tool environment/temperature variations. With a highly reflective, cold walled chamber, radiant heat from the halogen lamps is focused directly and predominantly on the material sample. As a result of the cold walled chamber, background desorption from the chamber wall is minimized during an out gassing measurement.

Film shrinkage is customarily measured using a spectrometer or ellipsometer, by measuring the film thickness of a wafer at room temperature, before and after a thermal process. While this approach is satisfactory, it would not determine the rate of film shrinkage at the various temperatures, nor would it provide information as to whether there are abrupt changes of thickness at certain temperatures. By incorporating a spectrometer that monitors film thickness changes in situ, through an optical window on top of the chamber, the invention is able to extract information about the rate of material losses and whether there are distinct thermal load limitations on the materials under study. This integrated in situ approach to material characterization overcomes the uncertainty in experimental interpretation due to sample to sample and tool to tool variations.

The invention may be used up to 500° C. without a cooling system. One embodiment includes a chamber cooling system which circulates cold water through channels drilled through the top plate and chamber body. Water flow for cooling is monitored by a flow meter which is connected to safety interlocks and a warning light which warns of little or no water flow of the specified flow required, generally less than one gallon per minute. Cooling helps to stabilize and remove heat generated from the halogen lamp source to the sample wafer, to prevent chamber overheating and to reduce background emission of gases or particulates by the chamber during a temperature cycle.

Figure 5:
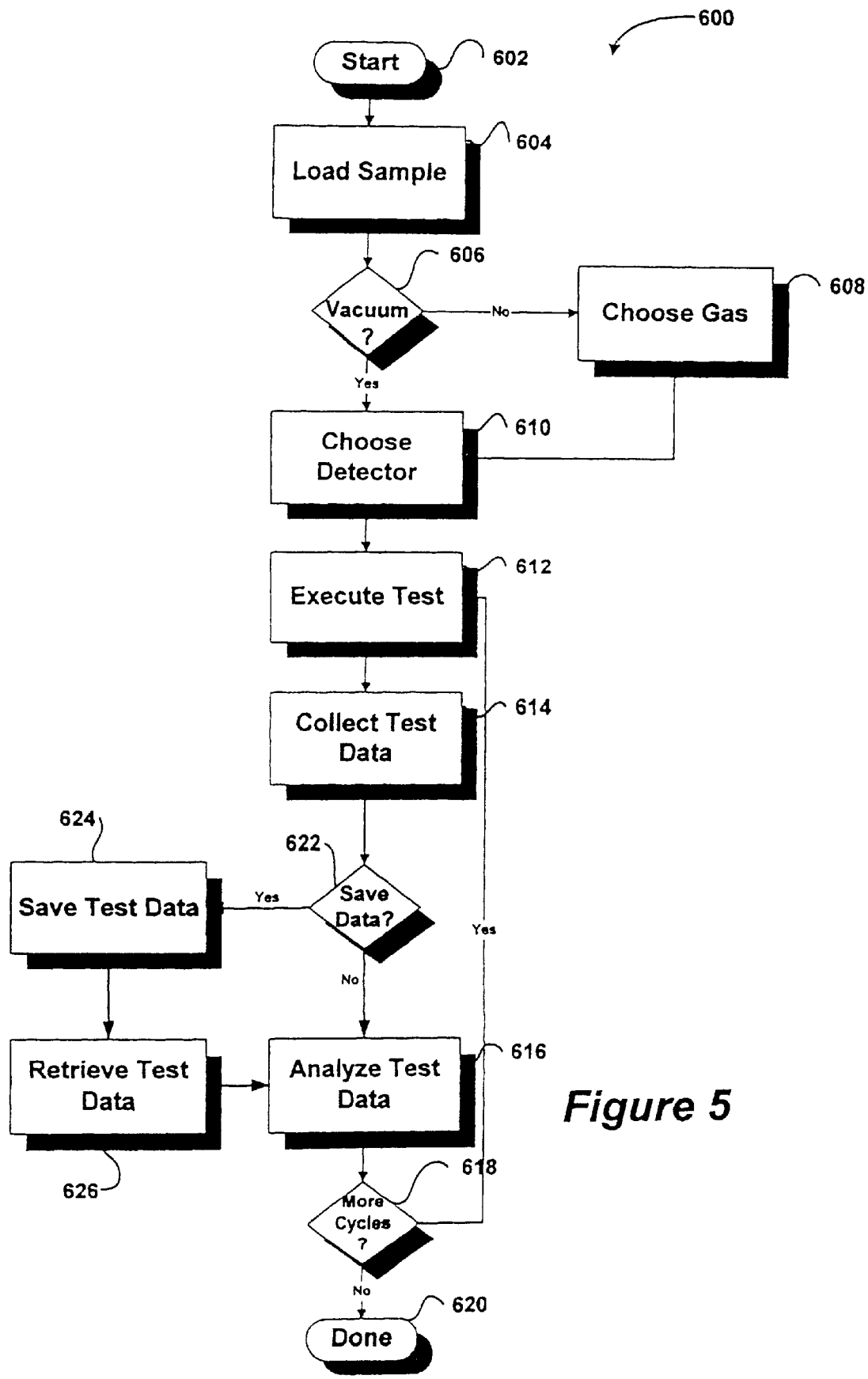
FIG. 5 is a flowchart showing a method for testing material properties in situ, in accordance with one embodiment of the present invention.

FIG. 5 is a flowchart showing a method 600 for testing material properties in situ, in accordance with one embodiment of the present invention. In an initial operation 602, pre-process operations are performed. Pre-process operations include calibrating the integrated sensors, and other pre-process operations that will be apparent to those skilled in the art.

In loading operation 604, a sample is loaded into the testing chamber. As stated previously, samples are generally placed on a fixed or rotatable susceptor made of quartz or a temperature stable material, supported and rotated by a quartz shaft, with an outer ring for temperature uniformity of the sample material.

A decision is then made as to whether the test environment will be a vacuum environment or a gas environment, in operation 606. For example, to collect outgasing data it is often necessary to perform the material test in a vacuum environment. If a gas environment is to be used the method 600 continues with a gas choice operation 608. However, if a vacuum environment is to be used, the method continues with a detector choice operation 610.

In a gas choice operation 608, a gas environment is selected. The present invention is capable of simulating various gas environments for material testing. In this operation, the user determines which gas environment will be utilized for the current material test. The user then selects the appropriate gas for the material test, and the method continues with the detector choice operation 610. Generally, inert gases such as nitrogen are used in the testing environment. However, other gases, such as oxygen, may be utilized as is necessary to simulate the processing environment wherein the material will eventually be used.

In a test type choice operation 610, test types are chosen. In this operation the user determines the exact test conditions or "recipe" under which the material will be tested. Generally, the user determines the type of test that will be performed, for example testing for shrinkage. Then the hardware is tuned by priming, typically at room temperature, the probes used in the test to ensure they are functioning correctly. The user then sets the integrated testing apparatus to simulate those conditions, as described in greater detail subsequently.

Next, in an execution operation 612, the actual test is started. Typically this operation includes evacuating the testing chamber and backfilling the chamber with the selected gas, or no gas when testing in a vacuum environment. In addition, when using a load-lock mechanism as a prechamber, both the prechamber and the testing chamber are evacuated and backfilled with the selected gas during this operaiton.

Test data is then collected in a collection operation 614. As stated previously, the present invention can operate either under high vacuum ranging up to 10–6 Torr or in a controlled inert gas environment to simulate device processes. In addition, by incorporating multiple metrology probes either inside the chamber or which can view the material sample inside the chamber, through an optical window, data like film stress hysteresis, thermal stability, thermal desorption spectroscopy, film shrinkage, reflectivity, resistivity and CV changes may be monitored in situ simultaneously.

A decision is made whether to save the collected test data, or to immediately analyze the collected test data in a step 622. Under some circumstances, such as when researching a possible new material, it may be desirable to save the test data for later analysis. This will lead to a save data step 624, discussed below. In other circumstances, such as normal processing operation, it may be desirable to simply analyze the data immediately to verify that the process is operating under acceptable parameters. In such cases, the analysis operation 616 immediately follows the collection operation 614.

If the data is to be saved, a save data step 624 stores the collected test data for later use. The data can be stored on a hard disk drive, or another device known to those in the art. When the time comes to analyze the stored data, a retrieve data step 626 retrieves the stored collected test data.

Then, in an analysis operation 616, the collected data is analyzed. Part of the data analysis performed by the present invention is data correlation. Data correlation allows a more accurate determination of the actual characteristics of a material than does uncorrelated single property data analysis, as described in greater detail subsequently. Data analysis in the present invention can be done using individual graphs produced by the system, or in overlay form, wherein the individual graphs are overlaid on one another to more easily correlate that test data. Thus, trends and changes in data between various tools are easy to determine.

A decision is then made as to whether more testing cycles are required before test completion, in operation 618. For example, to determine if a material is stable after thermal testing, it is often necessary to complete multiple cycles of testing before the material can be determined to be stable. If more testing cycles are required to complete the current test, the method 600 continues with the execution operation 612 where another test cycle is executed. However, if no more testing cycles are required for the current material test, the method 600 continues with operation 620, wherein post-process operations are performed. Post-process operations include filling the chamber and prechamber with gas and other shutdown procedures that will be apparent to those skilled in the art.

Figure 6:
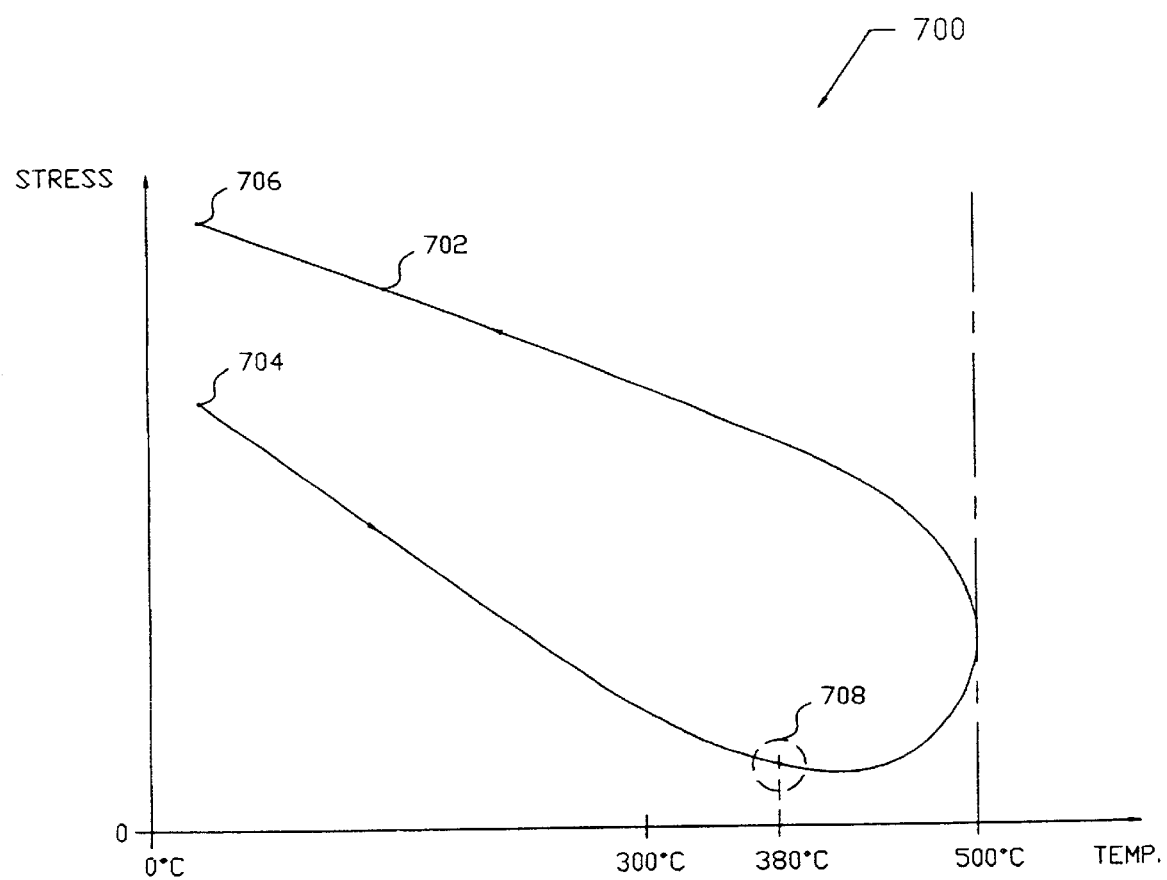
FIG. 6 is a graph showing a material stress hysteresis profile produced by one embodiment of the present invention using an in situ high temperature stress machine.

FIG. 6 is a graph showing a material stress hysteresis profile 700 produced by one embodiment of the present invention. The stress hysteresis profile 700 includes a material stress curve 702 having a start point 704 and an endpoint 706. As seen in the stress hysteresis profile 700, the material stress curve 702 has an essentially linear aspect from the start point 704 to a first inflexion point 708, indicating the material is essentially stable until the temperature in the testing chamber reaches about 380° C. At the inflexion point 708 the material begins to behave differently. Then at about 500° C. the chamber was allowed to cooled down to its starting temperature. However, as seen by the endpoint 706, the material has been irreversibly changed during the heating process.

The change in material behavior at the inflexion point 708 is due to one of several factors. Loss of material during the heating process may be due to outgasing. There can be shrinkage of material with or without outgasing. The only way to determine the reason for this behavior is by performing additional tests and correlating the resulting test data.

Figure 7:
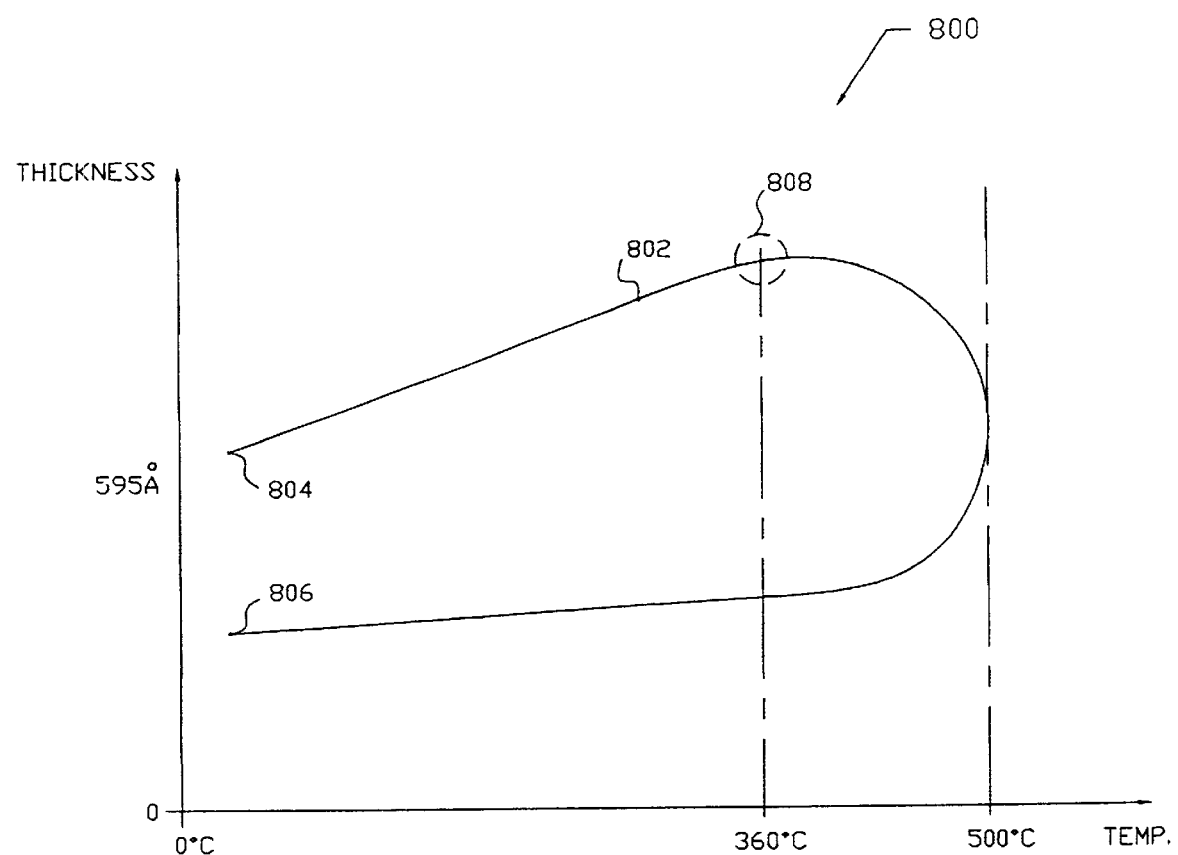
FIG. 7 is a graph showing a material shrinkage profile 800 produced by one embodiment of the present invention using an in situ film thickness monitor to examine shrinkage.

FIG. 7 is a graph showing a material shrinkage profile 800 produced using an in situ film thickness monitor to examine shrinkage. The material shrinkage profile 800 includes a material shrinkage curve 802, a start point 804, and an endpoint 806. The material shrinkage curve 802 increases from the start point 804 to a point of inflexion 808, as is expected due to thermal expansion. However, at the inflexion point 808 the material shrinkage curve decreases, at about 360° C. The material continues to shrink even though the temperature is increasing. Then at about 500° C., the chamber was allowed to cooled down to its starting temperature. However, as seen by the endpoint 806, the material has been irreversibly changed during the heating process.

Figure 8:
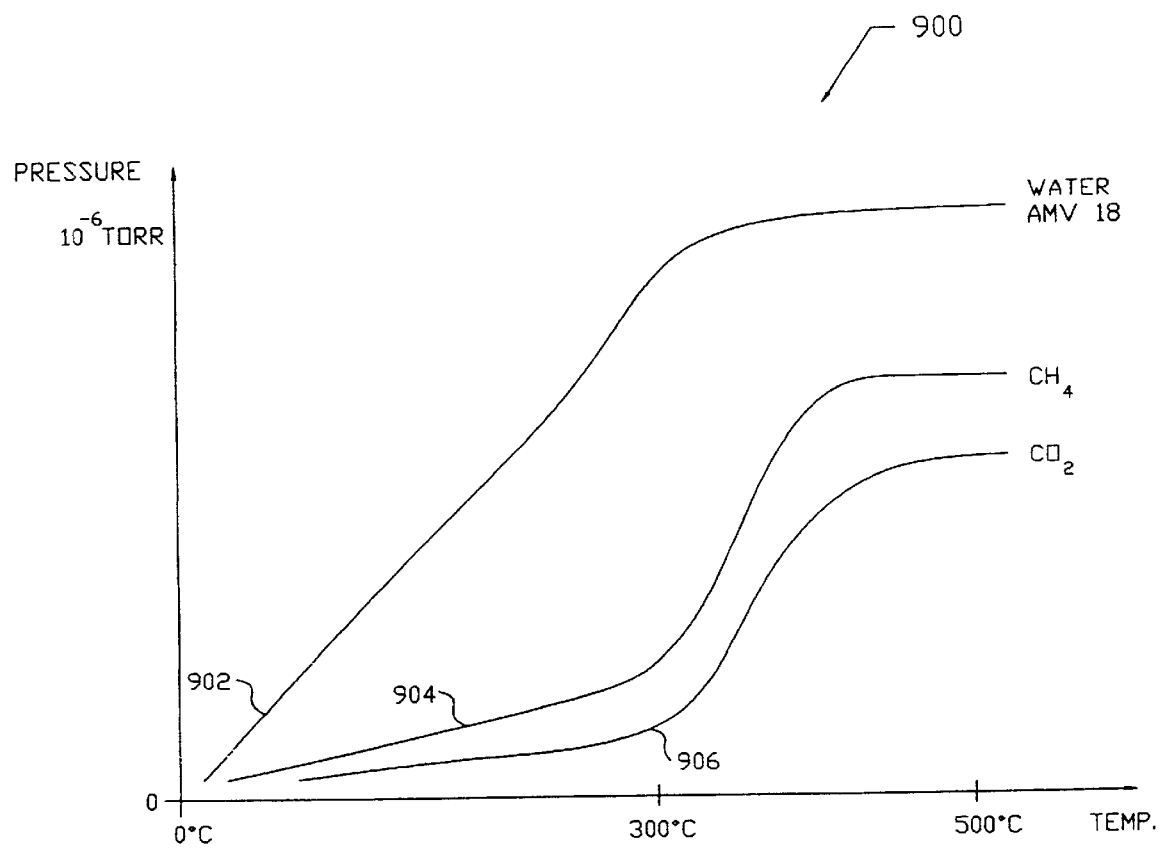
FIG. 8 is a graph showing gas pressure profile produced by an embodiment of the present invention using an in situ RGA/TDS machine.

FIG. 8 is a graph showing gas pressure profile 900 produced by one embodiment of the present invention using an in situ RGA/TDS machine. The gas pressure profile 900 includes an $H_2O$ gas curve 902, a $CH_4$ gas curve 904, and a $CO_2$ gas curve 906. As shown in the gas pressure profile, at about 300° C. there is an increase in gas pressure, thus confirming that there is an outgasing event. The data from FIG. 8 can be correlated with the data from FIG. 7.

Figure 9:
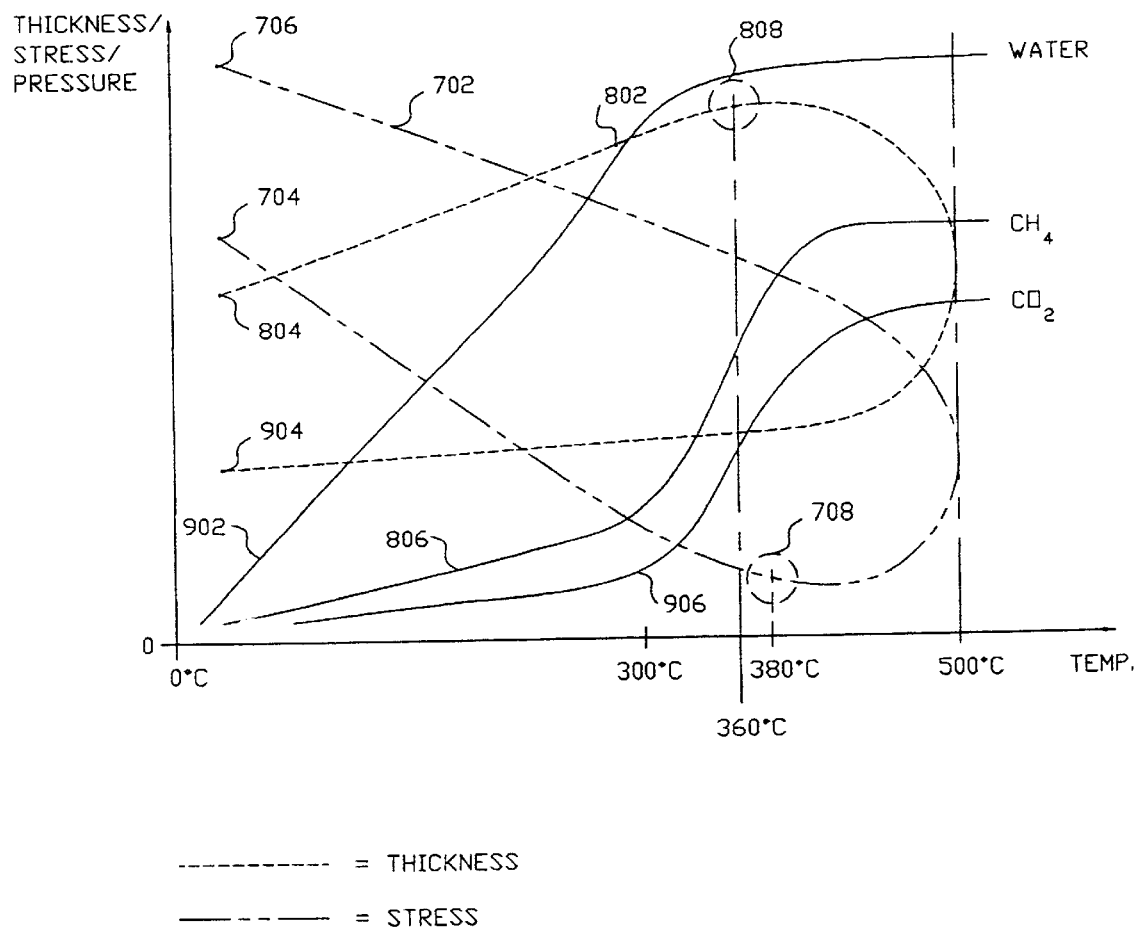
FIG. 9 is a graph correlating the data from the graphs in FIGS. 6–8.

FIG. 9 is a graph correlating the data from the graphs in FIGS. 6–8. By correlating the data from FIG. 6 and FIG. 7, FIG. 9 shows that the material thickness shrinkage in the shrinkage curve 802 is a physical event. The stress curve 702 shows that at about 380° C. the material begins to bend in the opposite direction of initial curvature. Correlating this with the shrinkage curve 802 shows that the material is smaller at this point. In other words, there is less material on the wafer hence mechanically there is less stress. Thus, the change in the shape of the wafer has been correlated to the physical shrinkage of material. However, the above-mentioned curves do not include enough information to determine if the material shrinkage is due to an actual loss of material. Thus, another test, outgasing, must be correlated.

By adding the graph of FIG. 8, which includes outgasing data, to the graphs of FIGS. 6 and 7, FIG. 9 allows the material characteristics of the material to be determined. From the gas curves 902, 904 and 906, it can be seen that outgasing begins at about 300° C., and material begins to leave the wafer. Then, as seen in the shrinkage curve 802, at about 360° C., enough material has been outgased that shrinkage occurs. Finally, as seen in the stress curve 702, at about 380° C. the shrinkage causes the wafer to physically bend in an opposite direction than its initial curvature. As shown in the gas pressure profiles 902, 904, and 906, at about 300° C. there is an increase in gas pressure, thus confirming that there is an outgasing event. Therefore, the shrinkage shown in the shrinkage curve 802 is due to an actual loss of material.

Figure 10:
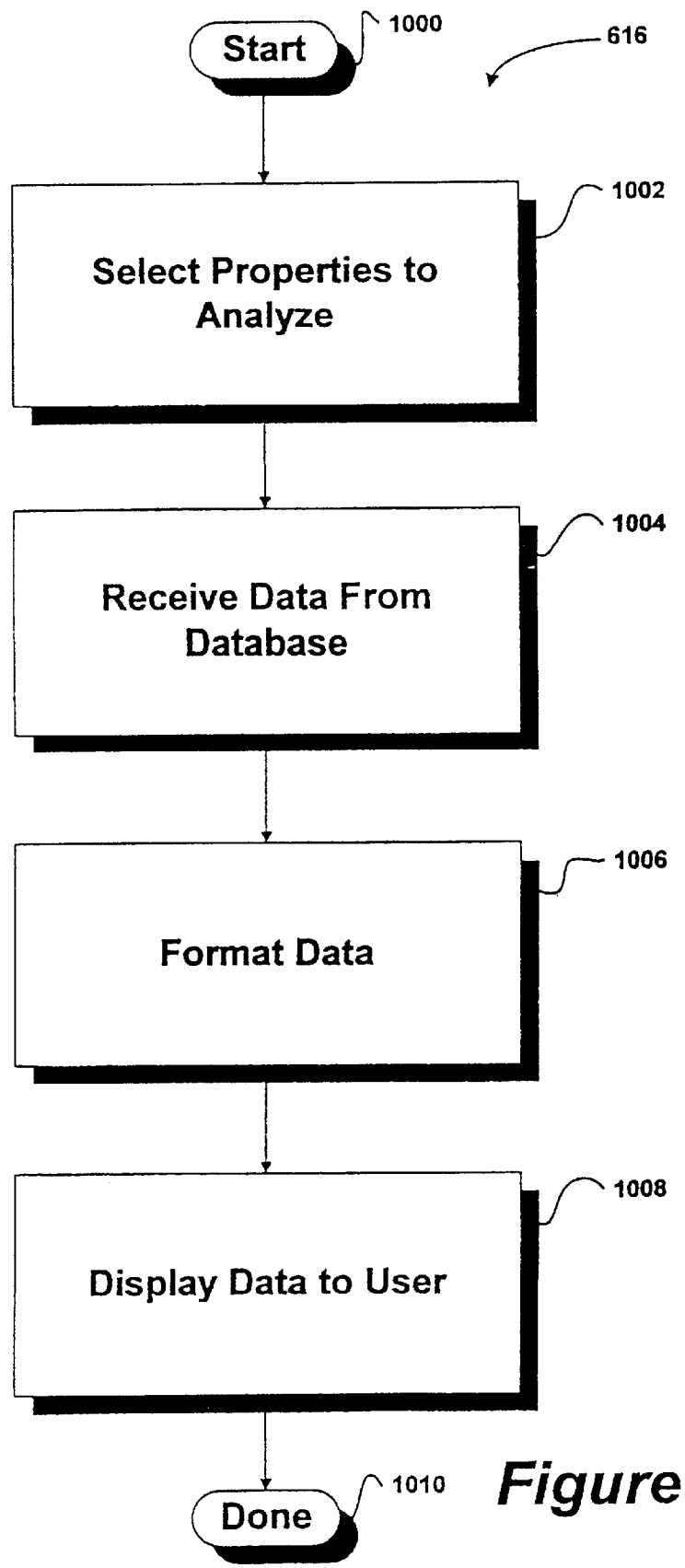
FIG. 10 is a flowchart showing a method for a user to analyze the data from tests performed.

FIG. 10 is a flowchart showing step 616 from FIG. 5 in more detail. FIG. 10 shows a method for a user to analyze the data from the multiple tests performed. The method begins in a step 1000. In a selection step 1002, the user decides which properties to analyze. For example, the user can select to analyze stress, as in FIG. 6, thickness, as in FIG. 7, outgasing, as in FIG. 8, or multiple properties, as in FIG. 9.

In a data-receiving step 1004, the data from the tests performed is received from a database. During testing, the sensors produce signals. Ordinarily, the signals are then fed through analog to digital converters to produce raw digital data and fed to the computer 8. The computer puts the digital data in multiple databases. At this point, the data consists essentially of raw numbers. These raw numbers are what are received in the data-receiving step 1004. At this point, if the user were to view the raw numbers, it would convey very little information. The data must be put in a form that will easily convey meaningful information to the user.

In a formatting step 1006, the raw data is formatted. That is, the raw data is correlated to the values and characteristics that were tested. The raw data is converted to a form that will provide meaningful information to a user. One format for the data is a chart or graph, such as those seen in FIGS. 6–9. Other formats can also be used, depending upon in how the user wants to view the test results.

In a display step 1008, the formatted data is displayed to the user. As discussed previously, the display step 1008 displays the formatted data to a user on a computer display. A common form of display is graphs. The user is able to view the graphs separately, or overlay the graphs to more easily see data correlations. Thus, the present invention uses a computer as a data correlator to correlate data received from various sensors, resulting accurate data correlation and material analysis. This display step allows the user to easily see the characteristics of the material, and how the material reacts under various process conditions. Since data from multiple tests can all be overlaid and viewed at once, users can easily correlate the data from multiple tests. One example of this is discussed above, in the discussion of FIG. 9. This gives users the advantage of more fully understanding the material being tested. Finally, after displaying the data, the method 616 ends in a step 1010.

Thus, the present invention provides a new integrated metrology tool for in situ material characterization. The invention utilizes a high temperature chamber, which can simulate the high vacuum or inert gas environment of low k and copper processes. Various probes and sensors are placed within and/or around this chamber for simultaneous extraction of thermal, mechanical, optical, chemical and electrical changes in the thin film, upon a thermal cycle or annealing process. Information such as stress hysteresis, out gassing, thermal desorption spectroscopy, film shrinkage, film reflectivity, resistivity and CV changes as a function of temperature or time can be collected simultaneously. Such an integrated approach overcomes the shortcomings of sample to sample and tool to tool variations that are inevitable in new material characterization. Therefore the screening, evaluation and integration of potential films, such as new low k and copper materials for next generation devices, may be accelerated.

To overcome these sample to sample and tool to tool variations, the integrated metrology tool of the present invention is able to simultaneously extract and display, in situ, several physical, optical, chemical and electrical properties changes during a heat cycle, or as a function of time.

While the present invention has been described in terms of several preferred embodiments, there are many alterations, permutations, and equivalents which may fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An apparatus for simultaneously extracting multiple physical characteristics of materials, comprising:
   a housing;
   a chamber disposed within said housing, said chamber being capable of achieving multiple temperatures, being capable of being filled with gases, and achieving a vacuum;
   material characteristic sensors disposed within said housing for providing at least a first set of data and a second set of data; and
   a data correlator coupled to said material characteristic sensors, said data correlator being capable of correlating said first set of data and second set of data.

2. An apparatus as recited in claim 1, wherein said chamber is capable of being back filled with gases of choice.

3. An apparatus as recited in claim 1 further comprising a chemical sensor.

4. An apparatus as recited in claim 1, wherein the material sample support stage and shaft is capable of rotation.

5. An apparatus as recited in claim 1, further comprising a sensor for detecting mechanical characteristics of a material sample.

6. An apparatus as recited in claim 1, further comprising a mechanical sensor.

7. An apparatus as recited in claim 1, further comprising a sensor for detecting optical characteristics of a material sample.

8. An apparatus as recited in claim 1, further comprising a sensor for detecting electrical characteristics of a material sample.

9. An apparatus as recited in claim 1, further comprising a sensor for detecting particulate characteristics of a material sample.

10. An apparatus as recited in claim 9, further comprising a sensor for detecting magnetic characteristics of a material sample.

11. An apparatus as recited in claim 1, further comprising a sensor for detecting temperature characteristics of a material sample.

12. An apparatus as recited in claim 1, said data correlator being operable to correlate inflection points of said first and second sets of data with variations in temperature.

13. An apparatus as recited in claim 1, wherein an interior surface of said chamber is plated with a highly reflective, inert material.

14. An apparatus as recited in claim 13, wherein the highly reflective, inert material is gold.

15. An apparatus as recited in claim 13, wherein the highly reflective, inert material is rhodium.

16. An apparatus as recited in claim 1, further comprising a prechamber connected to said chamber to allow transfer of samples from said prechamber to said chamber through an opening in the top of said chamber without exposing the samples to ambient atmosphere.

17. An apparatus as recited in claim 1, further comprising a display connected to said correlator, said correlator being operable to control the display to provide a graph of at least one of said sets of data.

18. An apparatus as recited in claim 17, said correlator being operable to control the display to overlay multiple graphs of said sets of data on said display, such that said display simultaneously displays more than one set of said sets of data.

19. A method for extracting and analyzing physical characteristics of materials, comprising the operations of:

providing a housing;

providing a chamber disposed within said housing, said chamber being capable of achieving multiple temperatures and a vacuum;

evacuating said chamber;

backfilling said chamber with a gas;

repeating the method until a desired degree of purity is achieved;

sensing a first set of physical properties of a sample material utilizing a first sensor disposed within said housing;

sensing a second set of physical properties of said sample material utilizing a second sensor disposed within said housing; and correlating said first set of physical properties and said second set of physical properties, whereby material characteristics of said sample material are determined.

20. A method as recited in claim 19, further comprising the operation of scanning the sample material with a scanning means to generate data signals.

21. A method as recited in claim 19, wherein the operation of scanning of the sample material comprises the operations of:

directing a laser beam onto a surface of the sample material along a scan line;

detecting a surface reflection of an incident signal;

detecting magnetic fields emanating from the sample material during thermal processing; and developing a data base for analysis and representation of selected characteristics of the sample material.

22. A method as recited in claim 19, further comprising the operation of conveying heat to said sample material utilizing a heat source;

providing a prechamber; and evacuating said chamber and said prechamber.

* * * * *